United States Patent

Berndt

[11] Patent Number: 5,869,329
[45] Date of Patent: Feb. 9, 1999

[54] BLOOD CULTURE VIAL OR BOTTLE HAVING AN AGITATION PADDLE

[75] Inventor: Klaus W. Berndt, Timonium, Md.

[73] Assignee: Becton Dickinson and Company, Franklin Lakes, N.J.

[21] Appl. No.: 918,033

[22] Filed: Aug. 25, 1997

[51] Int. Cl.⁶ .................................................. C12M 1/24
[52] U.S. Cl. ........................... 435/288.1; 435/288.2; 435/299.2; 435/304.1; 435/304.2; 604/416; 356/428; 215/DIG. 8; 422/102; 422/82.05
[58] Field of Search ................... 435/288.1, 288.2, 435/298.2, 299.1, 299.2, 304.1, 304.2; 604/415, 416; 356/428, 39, 246; 215/DIG. 3, DIG. 8, 388, 400; 422/102, 82.05, 82.08; 366/214, 213, 225–228

[56] References Cited

U.S. PATENT DOCUMENTS

| | | | |
|---|---|---|---|
| 3,740,321 | 6/1973 | Pagano et al. | 435/298.2 |
| 3,853,712 | 12/1974 | House et al. | 435/299.1 |
| 4,808,184 | 2/1989 | Tepic | 604/56 |
| 4,829,004 | 5/1989 | Varani et al. | 435/304.2 |
| 5,217,875 | 6/1993 | Kerpf et al. | 435/34 |
| 5,240,322 | 8/1993 | Haber et al. | 366/130 |
| 5,518,923 | 5/1996 | Berndt et al. | 435/287.3 |
| 5,549,574 | 8/1996 | Townsend | 604/232 |

FOREIGN PATENT DOCUMENTS

92/09681  6/1992  WIPO ............................ 435/288.2

*Primary Examiner*—William H. Beisner
*Attorney, Agent, or Firm*—Alan W. Fiedler

[57] ABSTRACT

The present invention describes a blood culture vial and bottle having an agitation paddle that enhances liquid agitation within the container, when the container is rotated on a turntable instrument. In particular, a flexible paddle is inserted into the container and is slightly oversized to be held in position within the container. In addition, the agitation paddle can have a variety of structures including a star shape or a helix shape.

16 Claims, 6 Drawing Sheets

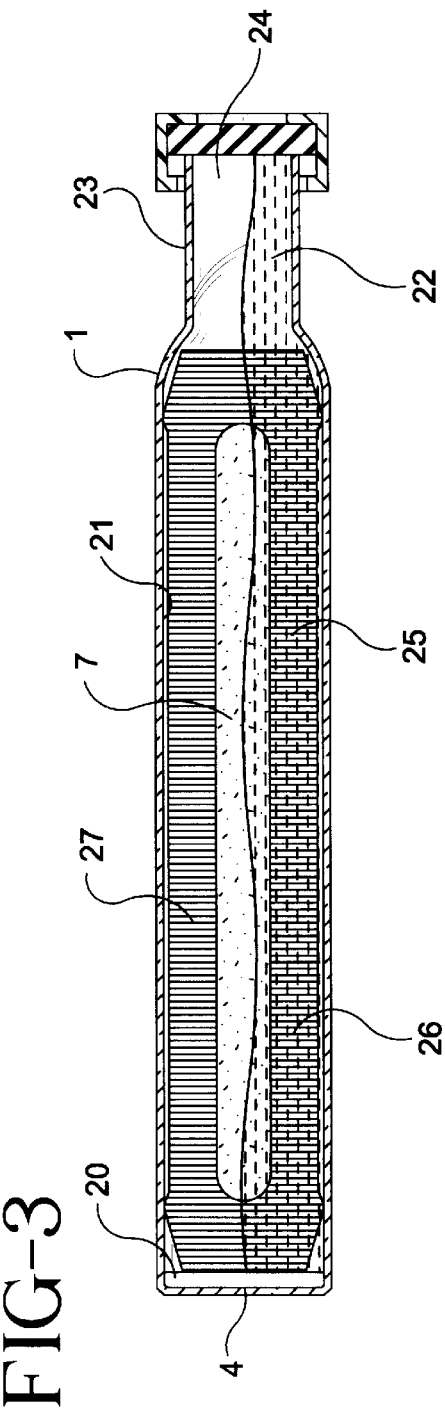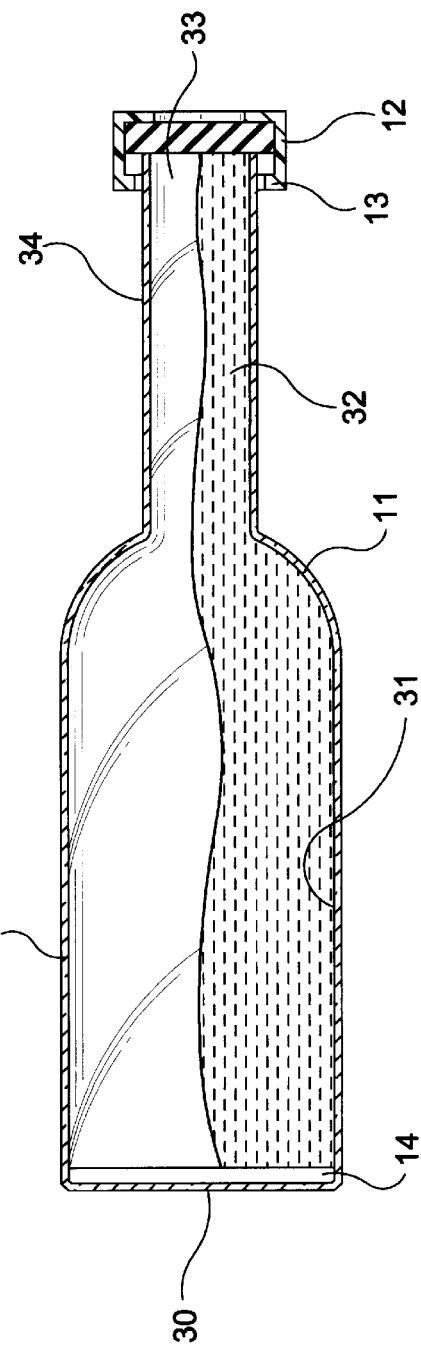

BLOOD CULTURE VIAL OR BOTTLE HAVING AN AGITATION PADDLE

BACKGROUND OF THE INVENTION

1. Field of the Invention

The present invention relates to a non-invasive apparatus for detecting and identifying microorganisms in a specimen such as blood, where the specimen and a culture medium are introduced into a large number of sealable blood culture vials and are exposed to conditions enabling a variety of metabolic, physical, and chemical changes to take place in the presence of microorganisms in the sample. These changes are monitored using colorimetric or fluorescent chemical sensors that are disposed on the inner bottom surface of each blood culture bottle.

2. Background Description

The presence of biologically active agents such as bacteria in a patient's body fluid, especially blood, is generally determined using blood culture containers. A small quantity of blood is injected through an enclosing rubber septum into a sterile container containing a culture medium, and the container is then incubated at 37° C. and monitored for microorganism growth.

One of the techniques used to detect the presence of microorganisms includes visual inspection. Generally, visual inspection involves monitoring the turbidity or eventual color changes of the liquid suspension of blood and culture medium. Known instrumental methods detect changes in the carbon dioxide content of the culture bottles, which is a metabolic by-product of the bacterial growth. Monitoring the carbon dioxide content can be accomplished by methods well established in the art, such as radiochemical or infrared absorption at a carbon dioxide spectral line. Until now, these methods have required invasive procedures which result in the well-known problem of cross-contamination between different containers. It has also been proposed to detect microorganism growth in sealable containers by monitoring positive and/or negative pressure changes.

Recently, non-invasive methods have been developed involving chemical sensors disposed inside the container. These sensors respond to changes in the carbon dioxide concentration by changing their color or by changing their fluorescence intensity. In known automated non-invasive blood culture systems, individual light sources, spectral excitation/emission filters, and photodetectors are arranged adjacent to each container. This results in station sensitivity variations from one container to the next. Therefore, extensive and time-consuming calibration procedures are required to operate such systems. In addition, flexible electrical cables are required to connect the individual sources and detectors with the rest of the instrument. With the large number of light sources, typically 240 or more per instrument, maintenance can become very cumbersome and expensive when individual sources start to fail.

In known colorimetric or fluorometric instruments, light emitting diodes ("LEDs") are used as the individual light sources. These sources have only a relatively low optical output power. Therefore, high photometric detection sensitivity is required to monitor the container sensor emissions. This results in additional and more complicated front-end electronics for each photodetector, increasing production cost. To reduce equipment cost and complexity, it has been proposed to use optical fibers at each container to feed the output light of an instrument's sensors to a central photodetector. A disadvantage to this approach is the need for arranging a large number of relatively long fibers of different length within the instrument.

In U.S. Pat. No. 5,518,923 it has been proposed to arrange a multitude of blood culture bottles on a rotating turntable with sensor stations mounted behind the turntable such that the sensor stations can monitor the bottles. In particular, as the turntable rotates, each bottle pass a sensor station and is interrogated for microorganism growth. It has also been proposed to perform a presumptive microorganism identification by monitoring more than one analyte per vial and analyzing the time behavior of the corresponding growth curves. (See U.S. Pat. No. 5,217,875.) However, in practice it has been found that with vials placed on a rotating turntable, the agitation of the liquid is insufficient and results in diffusion-limited growth curves. In other words, the time behavior of the growth curves is dominated by the size of the gas-liquid interface and the sensor response time, and only to a lesser degree by the metabolic characteristics of the microorganism population which can be a problem if organism identification is being attempted via growth curve analysis.

SUMMARY OF THE INVENTION

The present invention overcomes the above problems of the prior art by providing means for enhancing liquid agitation in blood culture vials in turntable instruments.

According to the present invention, the above objective is achieved by introducing a culture medium and the blood specimen into each sealable glass vial that comprises optical sensing means, and by introducing a flexible paddle into the vial, whereby the paddle is slightly oversized and is therefore held in a fixed position within the vial after its introduction due to its elastic deformation by the vial.

Other aspects, features and advantages of the present invention will become apparent from the following detailed description, taken in conjunction with the accompanying drawings.

DESCRIPTION OF THE DRAWINGS

FIG. 3 shows a cross-section of the pediatric blood culture bottle shown in FIG. 1 with a paddle according to FIG. 2 introduced;

FIG. 4 shows a cross-section of a standard blood culture bottle with a chemical sensor disposed to the inner bottom;

DETAILED DESCRIPTION

Figure 1:
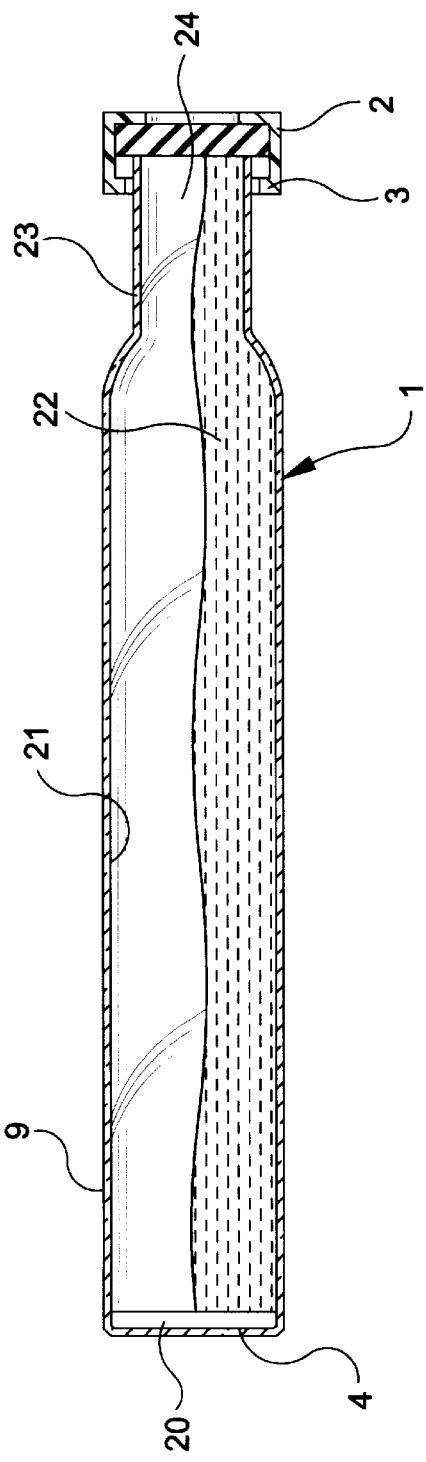
FIG. 1 shows a cross-section of a pediatric blood culture vial with a chemical sensor disposed to the inner bottom.

FIG. 1 shows a cross-section of a pediatric blood culture vial 1 having a base portion 9 with a chemical sensor 4 attached to its inner bottom 20 and a neck portion 23 having an opening 24. Chemical sensor 4 is provided to sense a chemical activity taking place within vial 1 and, in particular, can be a conventional chemical sensor 4 that responds to changes in the carbon dioxide concentration or oxygen concentration generated or consumed by microorganisms contained within vial 1. For example, chemical sensor 4 could be a colorimetric sensor or a fluorometric sensor. As shown in FIG. 1, a culture medium and blood specimen 22 could be introduced into vial 1 and then sealed therein by a piercable septum 2 and a cap 3.

Figure 2:
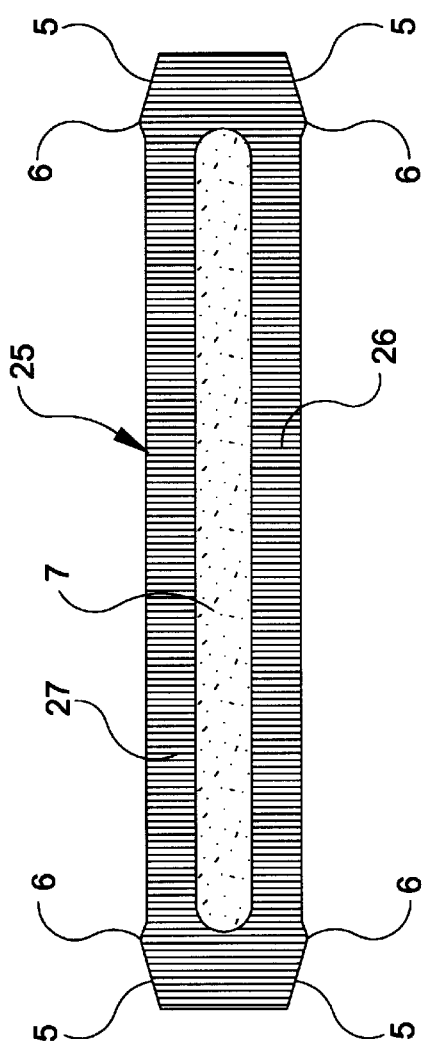
FIG. 2 depicts one possible form of a flexible paddle for use in the pediatric blood culture vial shown in FIG. 1.

FIG. 2 depicts one possible form of a flexible paddle 25 for use in the pediatric blood culture vial 1 shown in FIG. 1. Paddle 25 is made out of a flexible flat material, such as plastic, that can be sterilized. In order to make introduction of paddle 25 into blood culture vial 1 easy, paddle ends 5 on paddle 25 form the sides of a trapezium. A central slit 7 in paddle 25 provides sufficient flexibility during the introduction step and, additionally, acts as a pathway for the liquid media during vial rotation on a turntable. Each corner 6 on paddle 25 provides four well-defined contact areas between paddle 25 and walls 21 of blood culture vial 1. FIG. 3 shows a cross-section of pediatric blood culture vial 1 with paddle 25 mounted therein together with the liquid culture media and blood specimen 22.

During rotation of a turntable with ordinary vials, the liquid mixture has a tendency to stay in a fixed position. This results in a reduced mixing efficiency for the head space gas and the liquid. Entry of gas into the liquid is dominated by diffusion. With paddle 25 mounted in vial 1, however, the liquid is shoveled around within vial 1. On one side 26 of paddle 25, liquid is lifted until it falls through central slit 7 to the other side 27 of paddle 25. The other side of paddle 25 presses liquid downwards and enhances the turbulent flow. Lifting takes place twice per vial rotation, i.e., twice per turntable rotation. Due to the fact that the rotational axis of the turntable is typically tilted by approximately twenty degrees (20°) from the horizontal axis, some of the lifted liquid falls through a gas volume after passing through central slit 7, which further enhances the gas exchange between the head space gas and the liquid.

Figure 5:
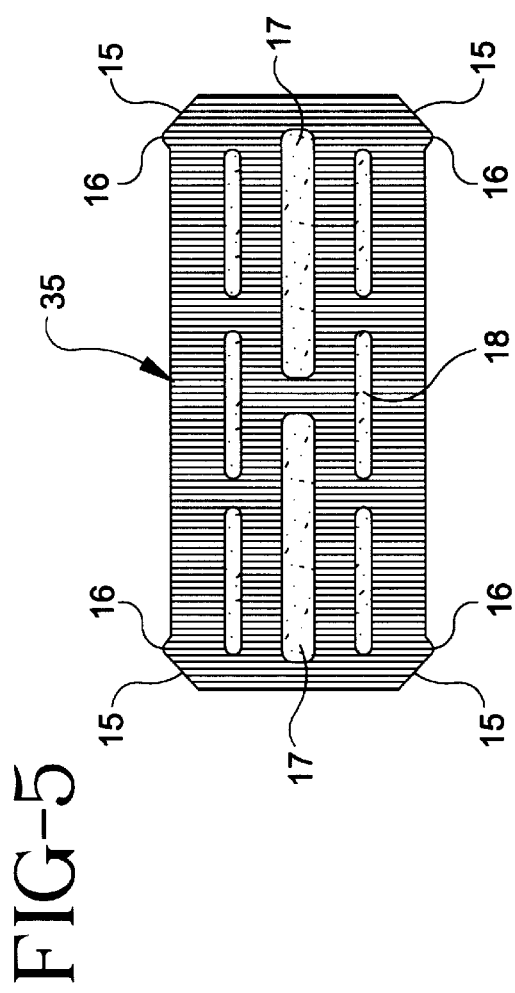
FIG. 5 depicts one possible form of a flexible paddle for use in the standard blood culture bottle shown in FIG. 4.
Figure 6:
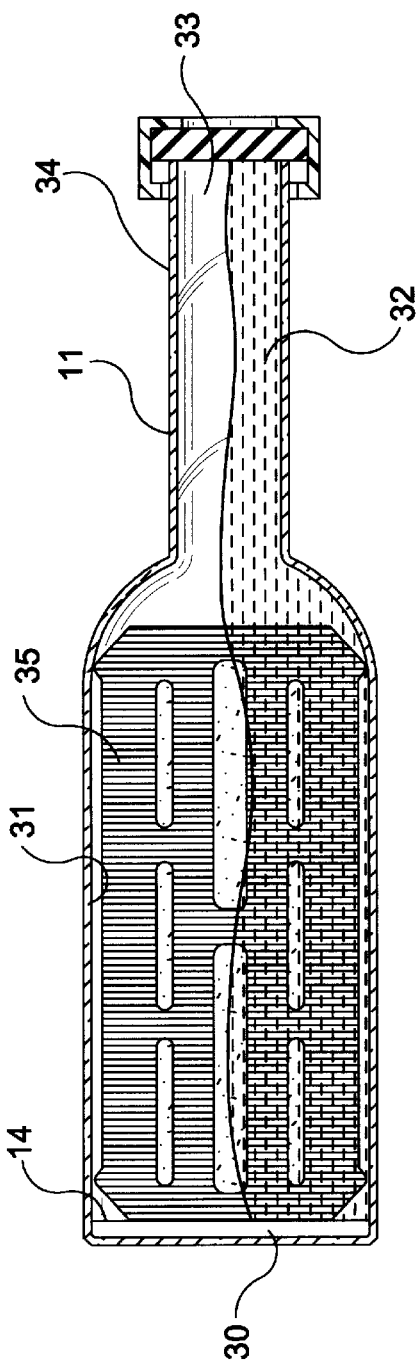
FIG. 6 shows a cross-section of the standard blood culture bottle shown in FIG. 4 with a paddle according to FIG. 5 introduced.

FIG. 4 shows a standard blood culture bottle 11, designed specifically for adult use. Bottle 11 has an opening 33 at its neck portion 34 sealed, as shown in FIG. 4, by a septum 12 and a cap 13. Bottle 11 also includes optical sensing means 14 in a base portion 19 on its inner bottom 30 and contains a culture media and blood specimen 32. FIG. 5 depicts one possible form of a flexible paddle 35 for use in blood culture bottle 11, shown in FIG. 4. Paddle 35 is made out of a flexible flat material, such as plastic, that can be sterilized. In order to make introduction of paddle 35 into blood culture bottle 11 easy, paddle ends 15 form the sides of a trapezium. A pair of central slits 17 provide sufficient flexibility during the introduction step and, additionally, act as a pathway for the liquid media 32 to move during bottle rotation on a turntable. Additional slits 18 provide further flexibility to ease introduction of paddle 35 into bottle 11. Corners 16 on paddle 35 provide four well-defined contact areas between paddle 35 and walls 31 of the blood culture bottle 11. FIG. 6 shows a cross-section of blood culture bottle 11 with paddle 35 mounted therein with the liquid culture media and blood specimen 32.

Figure 7:
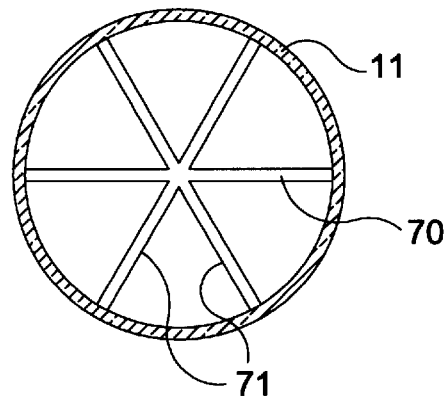
FIG. 7 shows a cross-section of a standard blood culture bottle similar to the one shown in FIG. 4 with a star shaped flexible paddle therein.
Figure 8:
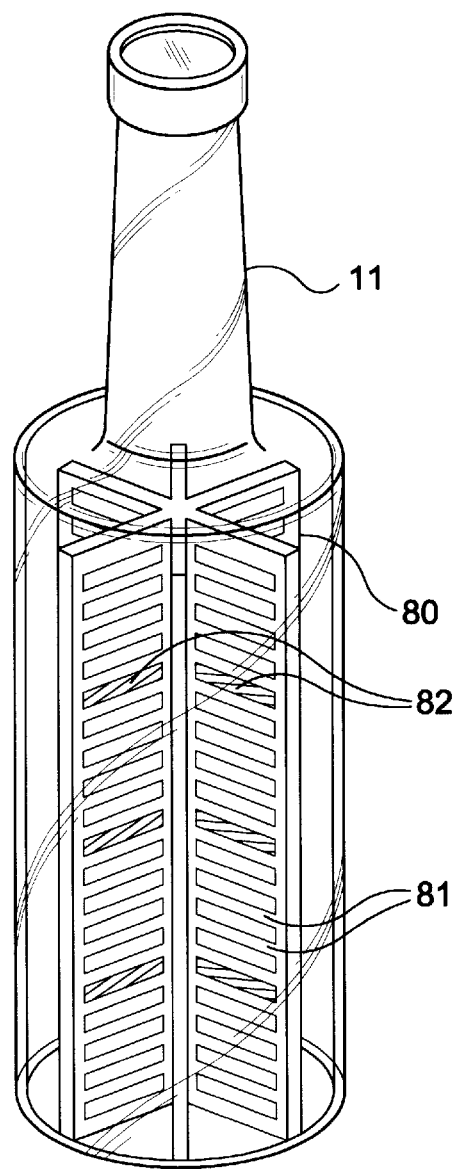
FIG. 8 shows a perspective view of a standard blood culture bottle similar to the one shown in FIG. 4 with a star shaped flexible paddle having a wheel of spokes.
Figure 9:
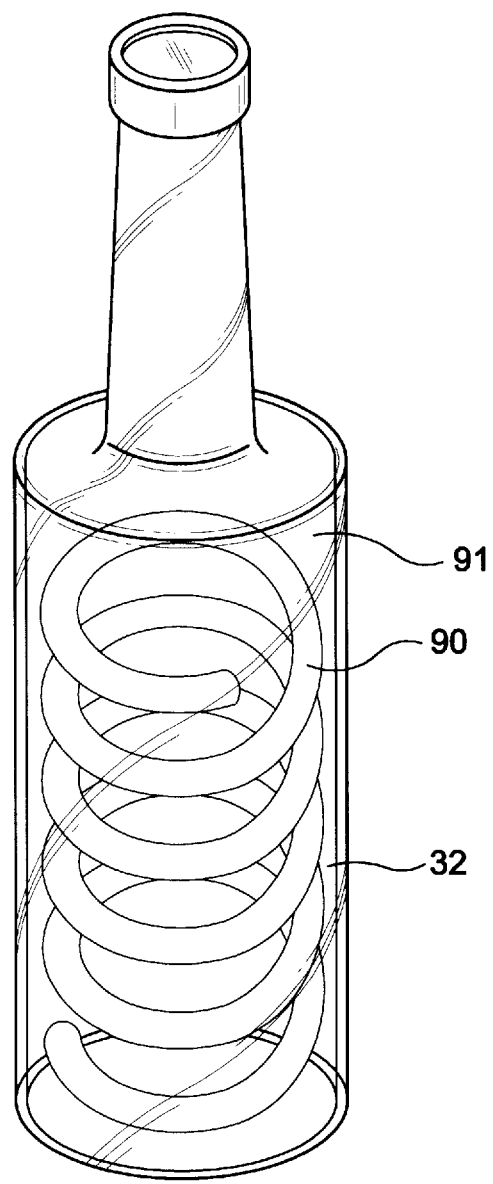
FIG. 9 shows a perspective view of a standard blood culture bottle similar to the one shown in FIG. 4 with a helix shaped flexible paddle.

Using flat material for paddles 25 and 35 allows for extreme low production cost. Due to the specific design, a self-centering process takes place after paddles 25 and 35 have been introduced into vial 1 and bottle 11, respectively. However, a paddle according to the present invention is not limited to the shapes depicted in FIGS. 2 and 5. Many different modifications are possible that would fall into the spirit of the invention. It would be possible, for instance, to select a different cross-section for the paddle if looking along the bottle axis, such as a star shaped paddle 70 having a plurality of paddle arms 71 (FIG. 7) or a star shaped paddle 80 having spokes 81 (FIG. 8). In one variation of a paddle according to the present invention shown in FIG. 9, paddle 90 has a helix structure which pumps the liquid media 32 into the head space region 91 during turntable rotation. Such a helix paddle 90 is easily introduced into bottle 11 even if opening 33 is significantly smaller than the inner diameter of bottle 11.

Figure 10:
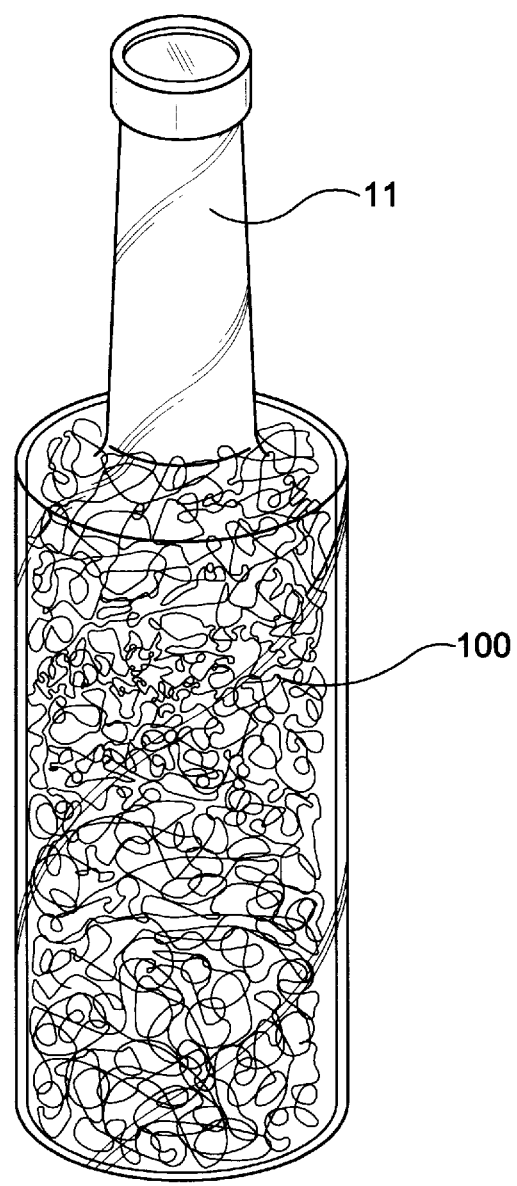
FIG. 10 shows a perspective view of a standard blood culture bottle similar to the one shown in FIG. 4 with a flexible paddle having a bird nest structure.

It is also possible to fill the interior of the bottle with a homogeneous material that has a structure like a bird's nest 100, shown in FIG. 10. In this case, paddle 100 is made of a material that would shovel liquid into the head space gas and/or head space gas into the liquid in a spatially more evenly process. It is also possible to utilize sections of the paddle introduced into a bottle for additional purposes such as carrying a sensor means or absorbing antibiotics. This is shown in paddle 80 which includes one or more sensor segments 82 between a number of the spokes 81.

While the invention has been described with respect to a number of preferred embodiments, it is apparent that various changes can be made without departing from the scope of the invention as defined by the appended claims.

What is claimed is:

1. A blood culture vial for holding a liquid, said blood culture vial comprising:

a base portion having a closed bottom surface;

a neck portion having a smaller diameter than said base portion and extending from said base portion to an opening;

a septum extending across said opening of said neck portion;

a cap holding said septum across said opening of said neck portion to provide a seal across said opening; and a paddle in said base portion of said blood culture vial for enhancing liquid agitation within said blood culture vial, when said blood culture vial is rotated, wherein said paddle includes a pair of ends that form the sides of a trapezium with each of said paddle ends having a pair of corners that provide the only contact between said paddle and said base portion of said blood culture vial.

2. A blood culture vial according to claim 1, wherein said paddle comprises a flexible flat material.

3. A blood culture vial according to claim 2, wherein said paddle further comprises a slit.

4. A blood culture vial for holding a liquid, said blood culture vial comprising:

a base portion having a closed bottom surface;

a neck portion having a smaller diameter than said base portion and extending from said base portion to an opening;

a septum extending across said opening of said neck portion;

a cap holding said septum across said opening of said neck portion to provide a seal across said opening; and a paddle in said base portion of said blood culture vial for enhancing liquid agitation within said blood culture vial, when said blood culture vial is rotated, wherein said paddle include a chemical senor.

5. A blood culture vial according to claim 4, wherein said paddle is comprised of a plurality of paddle arms arranged in the shape of a star.

6. A blood culture vial according to claim 5, wherein each of said paddle arms includes a plurality of spokes.

7. A blood culture vial according to claim 4, wherein said paddle is in the shape of a helix.

8. A blood culture vial according to claim 4, wherein said paddle comprises a homogeneous material having a bird nest structure.

9. A blood culture bottle for holding a liquid, said blood culture bottle comprising:

a base portion having a closed bottom surface;

a neck portion having a smaller diameter than said base portion and extending from said base portion to an opening;

a septum extending across said opening of said neck portion;

a cap holding said septum across said opening of said neck portion to provide a seal across said opening; and a paddle in said base portion of said blood culture bottle for enhancing liquid agitation within said blood culture bottle, when said blood culture bottle is rotated, wherein said paddle includes a pair of ends that form the sides of a trapezium with each of said paddle ends having a pair of comers that provide the only contact between said paddle and said base portion of said blood culture bottle.

10. A blood culture bottle according to claim 9, wherein said paddle comprises a flexible flat material.

11. A blood culture bottle according to claim 10, wherein said paddle further comprises a slit.

12. A blood culture bottle for holding a liquid, said blood culture bottle comprising:

a base portion having a closed bottom surface;

a neck portion having a smaller diameter than said base portion and extending from said base portion to an opening;

a septum extending across said opening of said neck portion;

a cap holding said septum across said opening of said neck portion to provide a seal across said opening; and a paddle in said base portion of said blood culture bottle for enhancing liquid agitation within said blood culture bottle, when said blood culture bottle is rotated, wherein said paddle includes a chemical sensor.

13. A blood culture bottle according to claim 12, wherein said paddle is comprised of a plurality of paddle arms arranged in the shape of a star.

14. A blood culture bottle according to claim 13, wherein each of said paddle arms includes a plurality of spokes.

15. A blood culture bottle according to claim 12, wherein said paddle is in the shape of a helix.

16. A blood culture bottle according to claim 12, wherein said paddle comprises a homogeneous material having a bird nest structure.

* * * * *